US00PP17303P2

(12) United States Plant Patent
Pierce

(10) Patent No.: US PP17,303 P2
(45) Date of Patent: Dec. 26, 2006

(54) ***CALIBRACHOA* PLANT NAMED 'CAL GOLDEY'**

(50) Latin Name: ***Calibrachoa* sp.**
Varietal Denomination: Cal Goldey

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 64 days.

(21) Appl. No.: 11/352,965

(22) Filed: Feb. 13, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Jondle & Associates P.C.

(57) ABSTRACT

A new *Calibrachoa* plant particularly distinguished by medium-sized, yellow-orange flowers with a red eye, early and continuous flowering, deep-green foliage with elliptical leaves, medium vigor, a bushy, low spreading to later prostrate or trailing and moderately compact plant habit, is disclosed.

2 Drawing Sheets

Genus and species: *Calibrachoa* sp.
Variety denomination: 'Cal Goldey'.

BACKGROUND OF THE NEW PLANT

The present invention comprises a new and distinct cultivar of *Calibrachoa,* botanically known as *Calibrachoa* sp., and hereinafter referred to by the cultivar name 'Cal Goldey'. The new cultivar originated from a hybridization made in October 2002 in Gilroy, Calif. The female parent was the proprietary light-red flowered *Calibrachoa* plant '501-1' (unpatented), while the male parent was the proprietary orange flowered *Calibrachoa* plant '508-1' (unpatented). The seeds produced by the hybridization were sown in May 2003 in Gilroy, Calif. A single plant selection was chosen for further evaluation and for asexual propagation in July 2003 in Gilroy, Calif.

The new cultivar was created in 2002 in Gilroy, Calif. and has been asexually reproduced repeatedly by vegetative cuttings and tissue culture in Gilroy, Calif. over a two-year period. 'Cal Goldey' has not been observed under all possible environmental conditions. The present invention has been found to retain its distinctive characteristics through successive asexual propagations.

Plant Breeder's Rights for this cultivar were applied for in Canada on Mar. 29, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium-sized, yellow-orange flowers with a red eye (a red ring around the flower opening);
2. Deep-green foliage with elliptical leaves;
3. Medium vigor and moderately compact plant habit;
4. A low spreading to later prostrate to trailing and bushy plant habit; and
5. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of whole plants about 11-weeks old, grown in a greenhouse in Hillscheid, Germany, in May of 2005.

DESCRIPTION OF THE NEW CULTIVAR

Figure 1:
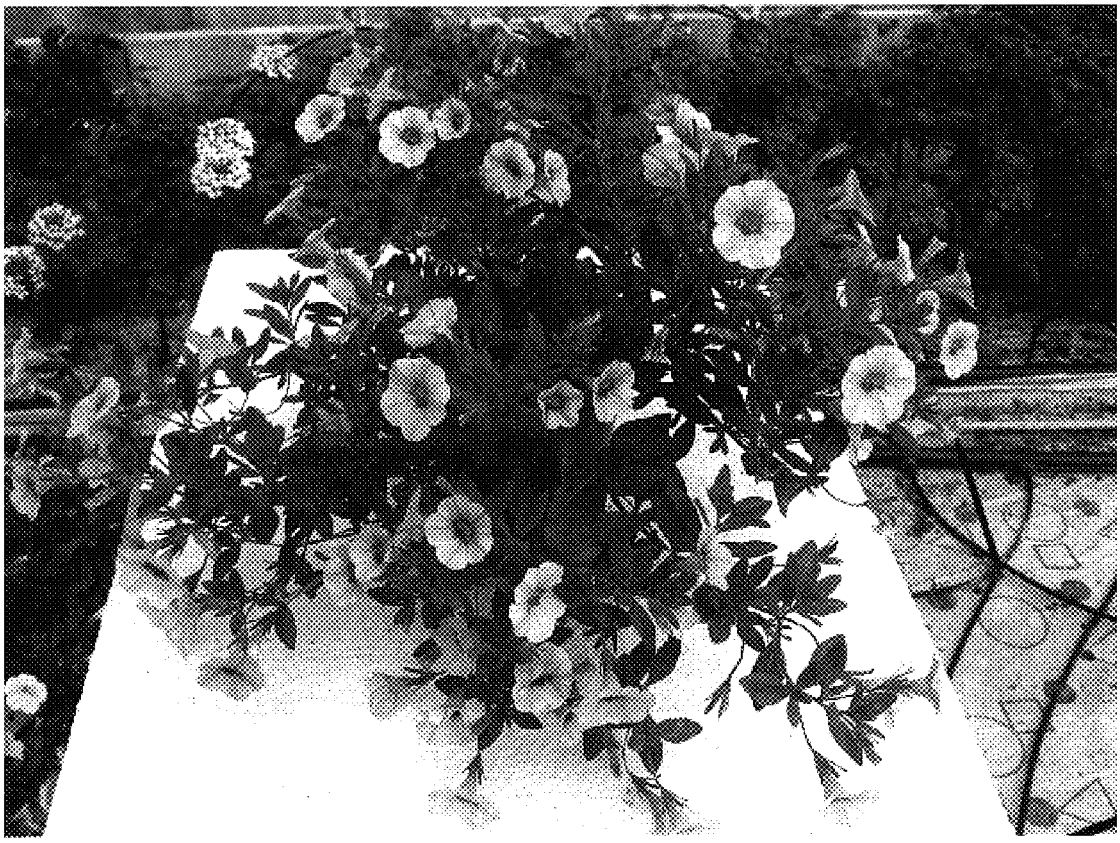
FIG. 1 shows the overall plant habit, including blooms, buds, and foliage.
Figure 2:
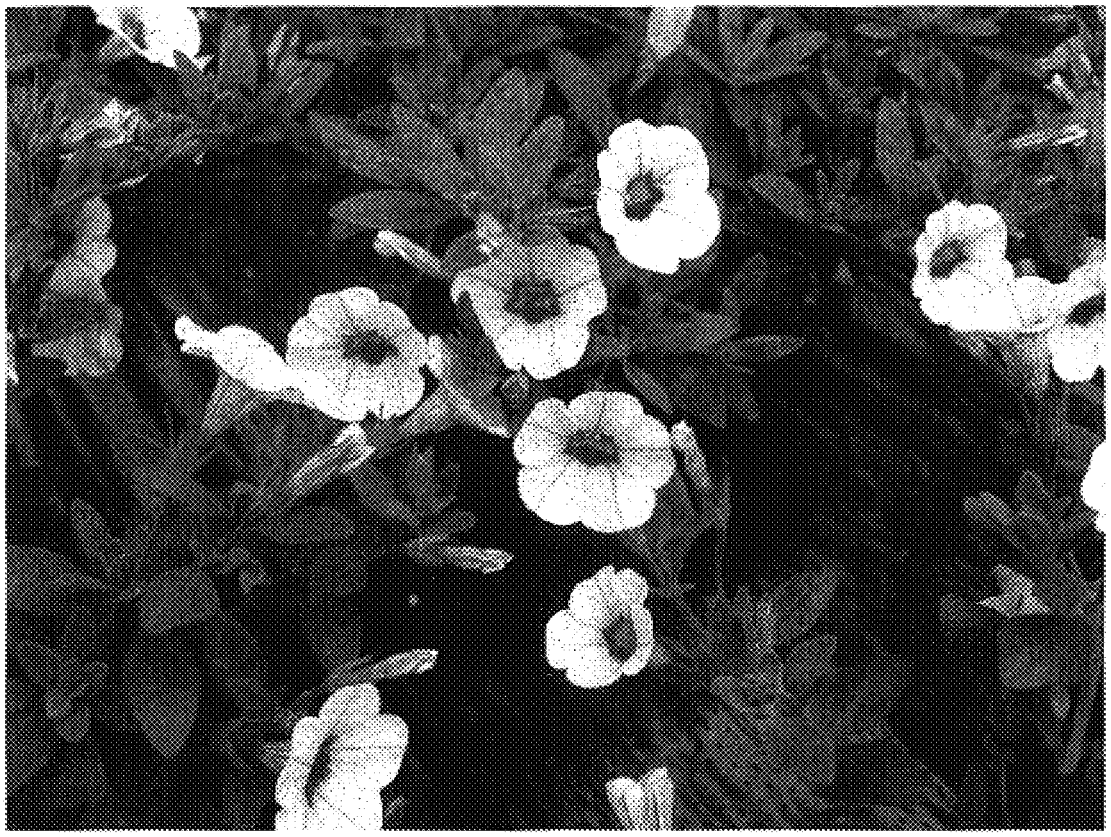
FIG. 2 shows a close-up of the mature inflorescences.

The following detailed description sets forth the distinctive characteristics of 'Cal Goldey'. The data which define these characteristics were collected from asexual reproductions carried out in Hillscheid, Germany. The plant history was taken on 6-week old unpinched plants which were planted as rooted cuttings in 12-cm pots in July 2005, and then grown in a greenhouse. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:
*Female parent.*—'501-1' a proprietary light-red flowered *Calibrachoa* plant (unpatented).
*Male parent.*—'508-1', a proprietary orange-flowered *Calibrachoa* plant (unpatented).

Growth:
*Form.*—Herbaceous perennial, usually cultivated as an annual plant.

*Habit.*—Spreading to prostrate, later trailing, with fair branching; should be pinched once to enhance basal branching.

*Height* (*measured from the top of the soil*).—12.1 cm.

*Width* (*horizontal plant diameter*).—34.2 cm.

*Propagation.*—Terminal tips for cuttings.

*Time to produce a finished flowering plant.*—9 to 10 weeks for a 12-cm pot.

*Outdoor plant performance.*—For hanging baskets and containers.

*Time to initiate and develop roots.*—About 24 days.

*Root description.*—Fibrous, self-branching.

Stems:

*Average number* (*basal plus secondary*).—10.8.

*Length of basal branches.*—21 cm.

*Internode length.*—1.5 cm to 2.5 cm.

*Diameter of branches* (*from midpoint*).—0.2 cm to 0.3 cm.

*Stem color.*—RHS 143C (green) towards the tip, RHS 174A (brown) from base to midpoint infused with anthocyanin.

*Texture.*—Somewhat rough with dense hair.

Leaves:

*Arrangement.*—Initially alternate, later opposite or nearly opposite on flowering branches.

*Size.*—Length: 3.5 cm to 5.5 cm. Width: 1.2 cm to 1.9 cm.

*Shape.*—Lanceolate.

*Margin.*—Entire.

*Apex.*—Acute to obtuse.

*Base.*—Attenuate.

*Color* (*mature leaves*).—Upper surface: RHS 137A to RHS 139A (deep-green). Lower surface: RHS 137D.

*Texture.*—Appears smooth and somewhat glossy, yet covered with very fine pubescence.

*Venation.*—Pinnate (indistinct).

*Venation color.*—RHS 145B (pale light-green) for mid-rib of lower surface.

*Variegation.*—None.

*Petioles.*—Cannot be clearly distinguished from the base of the leaf. Length: About 0.5 cm. Width: 0.2 cm. Color: RHS 145A for both sides. Texture: Pubescent.

Flower bud:

*Shape.*—Tube-shaped to narrow funnel-shaped.

*Size.*—Length: 2.2 cm. Diameter: 0.5 cm to 0.6 cm.

*Color at tight bud.*—RHS 12C (dull-yellow), RHS 22C for tips.

Inflorescence:

*Blooming habit.*—Continuous from Spring to Fall, nearly year-round.

*Inflorescence type.*—Flowers appear solitary, emerging from the leaf axil.

*Floret type.*—Base is funnel-shape; 5-lobed, lobes open outward, salver-shaped, somewhat zygomorphic.

*Number of flowers per node.*—1.

*Lastingness of individual blooms on the plant.*—6 days.

*Size.*—Width (flower face): 3.3 cm. Length (flower face): 2.9 cm. Depth (total length of flower): 2.0 cm to 2.3 cm. Funnel: Length (from below): 1.9 cm. Diameter (at opening): Up to 1.0 cm.

*Fragrance.*—Weak, petunia like.

*Peduncle.*—Color: RHS 143C (green). Length: 2.0 cm to 3.5 cm. Diameter: 0.1 cm. Texture: Dense pubescence.

Flowers:

*Immature flower.*—Diameter: 2.9 cm. Color: RHS 16A (orange-yellow).

*Mature flower color.*—Upper surface: RHS 13A to RHS 13B (golden-yellow), with an RHS 44A to RHS 45B (red) ring around the funnel opening; practically no veins apart from the RHS 23A (orange) line in the middle of the lobe. Lower surface: RHS 18B.

*Corolla.*—Shape of corolla: Lower-part tube-shaped. Color inside: RHS 12A (yellow). Color outside: RHS 162B (ochre-yellow). Outside texture: Appears rippled/furrowed lengthwise.

*Petals.*—Shape: Lower part is fused and upper part is a free lobe. Apex: Truncate. Base: Fused. Margin: Entire. Waviness of petals: Absent. Lobation: Weak to medium. Texture: Smooth.

*Sepals.*—Shape: Lanceolate. Apex: Acute to obtuse. Base: Fused. Margin: Entire. Length: 1.2 cm. Width: 0.2 cm to 0.3 cm. Color: RHS 143B (green). Texture: Covered by dense hair. Pubescence color: Whitish.

Reproductive organs:

*Stamens.*—Number: 5 (various lengths). Filament color: RHS 155A (whitish). Filament length: 1.0 cm to 1.5 cm. Filament diameter: 0.1 cm. Pollen color: RHS 8C (pale-yellow). Pollen quantity: Moderate.

*Pistils.*—Number: 1. Length: 1.4 cm. Diameter: 0.1 cm. Stigma color: RHS 145B (green). Style color: RHS 145C to RHS 145D (light-green).

Fruit and seed set: No seed set observed.

Disease and insect resistance: No particular resistance or susceptibility has been observed.

COMPARISON WITH PARENTAL AND COMMERCIAL CULTIVARS

'Cal Goldey' differs from the female parent '501-1' (unpatented) by having yellow-orange flowers with a red eye, while '501-1' has light-red flowers and no eye. In addition, 'Cal Goldey' develops more basal branches and has a more prostrate plant habit than '501-1'.

'Cal Goldey' differs from the male parent '508-1' (unpatented) by having yellow-orange flowers while '508-1' has orange flowers. In addition, 'Cal Goldey' has deeper green foliage and an earlier flowering response than '508-1'.

'Cal Goldey' differs from the commercial cultivar 'Sunbelki' (U.S. Plant Pat. No. 11,558) by having more golden-yellow flowers with red markings, while 'Sunbelki' has yellow flowers with a brown corolla tube. In addition, 'Cal Goldey' has a taller plant habit than 'Sunbelki'.

I claim:

1. A new and distinct cultivar of *Calibrachoa* plant as shown and described herein.

* * * * *